United States Patent [19]

Rahtz et al.

[11] 4,020,164
[45] Apr. 26, 1977

[54] BENZOMORPHAN DERIVATIVES

[75] Inventors: Dieter Rahtz; Eberhard Schroder; Reinhard Horowski; Gert Paschelke; Dieter Palenschat; Helmut Wachtel; Wolfgang Kehr, all of Berlin, Germany

[73] Assignee: Schering Aktiengesellschaft, Berlin & Bergkamen, Germany

[22] Filed: Feb. 18, 1975

[21] Appl. No.: 550,611

Related U.S. Application Data

[63] Continuation of Ser. No. 374,021, June 27, 1973, abandoned.

[30] Foreign Application Priority Data

June 30, 1972 Germany ............ 2233088

[52] U.S. Cl. ............ 424/267; 260/293.54; 260/DIG. 13
[51] Int. Cl.² ............ C07D 221/26; A61K 31/445
[58] Field of Search ............ 260/293.54; 424/267

[56] References Cited

UNITED STATES PATENTS

| | | | |
|---|---|---|---|
| 3,417,094 | 12/1968 | Dexter | 260/294.7 |
| 3,644,373 | 2/1972 | Kigasawa et al. | 260/293.54 |
| 3,723,440 | 3/1973 | Freter et al. | 260/293.54 |

OTHER PUBLICATIONS

Gulati et al., Indian J. Pharm. 27(7), pp. 195–197 (1965); Chem. Abstracts 63:10536a.

*Primary Examiner*—G. Thomas Todd
*Attorney, Agent, or Firm*—Millen & White

[57] ABSTRACT

Benzomorphans of the formula

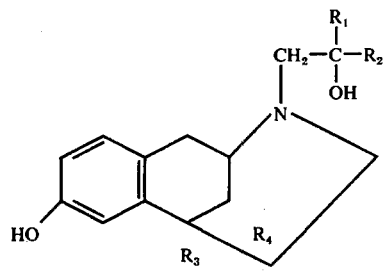

wherein $R_1$ is H, $CH_3$ or $C_2H_5$; $R_2$ is $CH_3$ or $C_2H_5$ and $R_3$ and $R_4$, which can be alike or different, each are lower alkyl, and the acid addition salts thereof with physiologically acceptable acids have CNS activity, including analgesic, morphine antagonistic, anti-convulsive, muscle relaxant, sedative and neuroleptic activity.

18 Claims, No Drawings

BENZOMORPHAN DERIVATIVES

This is a continuation, of application Ser. No. 374,021, filed June 27, 1973, now abandoned.

BACKGROUND OF THE INVENTION

This invention relates to novel benzomorphans and a process for their production.

SUMMARY OF THE INVENTION

The novel compounds of this invention are benzomorphans of the general Formula

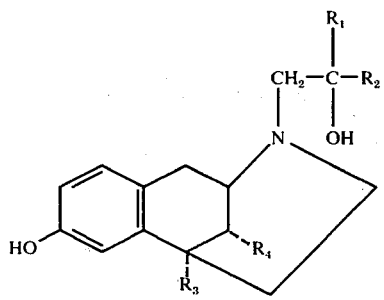

wherein $R_1$ is H, $CH_3$ or $C_2H_5$; $R_2$ is $CH_3$ or $C_2H_5$; and $R_3$ and $R_4$, which can be alike or different, each are lower alkyl, and the acid addition salts thereof with physiologically acceptable acids.

DETAILED DISCUSSION

The term "lower alkyl" means alkyl of 1–4 carbon atoms, e.g., methyl, ethyl, n-propyl, isopropyl, n-butyl, isobutyl.

The compounds of Formula I can be present as racemates as well as in the form of the optically active antipodes. They can be in free base form or as a pharmacologically acceptable acid addition salt, preferably the hydrochloride or hydrobromide.

Suitable for salt formation are physiologically compatible inorganic and organic acids. Such acids include, for example, mineral acids, e.g., hydrochloric, hydrobromic, sulfuric and phosphoric acid, and organic acids, e.g., acetic, propionic and other alkanoic acids, lactic acid, malonic acid, and other hydroxy and polybasic acids, including succinic acid, tartaric acid, citric acid, maleic acid, malic acid, heptagluconic acid, etc.

The novel compounds of general Formula I exhibit a profile of CNS activity, as evidenced by a combination of several valuable properties. They possess high analgesic potency, without producing morphine-like tolerance and physical dependence. They exert morphine-antagonistic, anti-convulsive and muscle-relaxant activity and have substantial sedative and neuroleptic properties. The novel compounds are characterized by a rapid onset of activity, both orally and parenterally.

In various neuropharmacological test methods, the novel compounds were found to be more potent than the conventional analgesic pentazocine, and equipotent or more potent than cyclazocine, another narcotic partial antagonist of the benzomorphan series with analgesic (J. Pharmacol. Exp. Ther. 144, 12, 1964) and antidepressant properties (Clin. Pharmacol. Ther. 11:1, 41, 1970). Furthermore, the novel compounds are more potent than chlordiazepoxide in protecting mice against electroshock, thus indicating a strong anti-convulsant and muscle-relaxant activity. The novel compounds are only slightly less active than haloperidol in alleviating stereotyped behavior in rodents under apomorphine, a characteristic of neuroleptic activity.

As evidenced by this spectrum of activities, the compounds of this invention are CNS-active compounds having a broad spectrum of therapeutic application. They are especially useful as analgesics, neuroleptanalgesics, neuroleptics, muscle-relaxant anti-convulsants, for the production of a "narcotic blockade," and as anti-depressants.

The pharmacological investigations were conducted on mice weighing 20–22 g. or on rats weighing 80–110 g. Unless indicated otherwise, the test substances were administered in the form of the hydrochloride acid addition salt thereof in an isotonic NaCl solution, and the animals were examined 30 minutes after subcutaneous (sc) application. The injection volume was respectively 5 ml./kg. of body weight. 10–40 controls animals were used in each experiment. The test and control solutions were administered in accordance with a randomized injection schedule. Seven logarithmically spaced dosages were employed of each test substance. The effective dose (ED) was calculated by probit analysis (Finney, D. J., "Probit Analysis," Cambridge University Press, 2nd Edition, Cambridge 1957). $ED_{50}$ figures were rounded.

The following compounds were involved in the tests described below.

Compound A: (−)-5-ethyl-2′-hydroxy-2-(2-hydroxy-2-methylpropyl)-9-methyl-6,7-benzomorphan Compound B: (−)-2′-hydroxy-2-(2-hydroxy-2-methylpropyl)-5,9-dimethyl-6,7-benzomorphan Compound C: (−)-5-ethyl-2′-hydroxy-2-(2-hydroxypropyl)-9-methyl-6,7-benzomorphan Compound D: (−)-2′-hydroxy-2-(2-hydroxypropyl)-5,9-dimethyl-6,7-benzomorphan.

Compounds A and B, when tesed in the writhing test procedure, a procedure for measuring the analgesic activity of narcotic partial antagonists (Nature 204, 189, 1964; Proc. Soc. Exp. Biol. Med. 118, 763, 1965), modified after the method of Siegmund et al. (Proc. Soc. Exp. Biol. 95, 729, 1957), are found to be at least equipotent with cyclazocine, more potent than morphine, and appreciably more potent than pentazocine. The novel compounds show a fast onset of activity, regardless of the manner of administration. After subchronic administration of equal total doses, the novel compounds and pentazocine, in contrast to morphine, do not exhibit tolerance development.

In the acute test, the test compounds were administered perorally (p.o.) or subcutaneously (s.c.) to mice. Eight mice were used per dose. Seven minutes prior to the testing, the animals received 2 mg./kg. of phenylquinone intraperitoneally. At ten and at thirty minutes resp., after the administration (p.i.) of the test substance, the animals were observed for writhes. The phenylquinone dosage employed corresponds to the $ED_{95}$ for the evocation of writhing with a maximum action within 10 minutes p.i. The criterion for protection effect was absence of writhes during the eighth minute after phenylquinone administration.

In the subchronic test, the same test was performed 25 hours after the last injection of a 64-hour pretreatment period, with the test compound being administered subcutaneously. During the pretreatment period, the subjects received a total of 550 mg/kg. of the test compound, with the test compound being injected over a period of 22 hours in 4 inceasing dosages in salt form, and over an additional 42 hours in 2 identical dosages in free base form in sesame oil.

The results of the writhing tests are summarized in Table 1 below.

TABLE 1

| | Writhing Test $ED_{50}$ (mg/kg) | | | | |
|---|---|---|---|---|---|
| | Acute | | | | Sub-chronic |
| | p.o. | | s.c. | | s.c. |
| Compound | 10 min. p.i. | 30 min. p.i. | 10 min. p.i. | 30 min. p.i. | 30 min. p.i. |
| A | 3 | 7 | 0.03 | 0.2 | |
| B | 5 | 10 | 0.05 | 0.4 | 0.4 |
| Cyclazocine | 6 | 8 | 0.06 | 0.09 | |
| Pentazocine | 50 | 70 | 3 | 3 | 4 |
| Morphine | 7 | 3 | 0.3 | 0.5* | 3 |

*Significant difference between acute and subchronic $ED_{50}$ (p < 0.001)

In order to determine the morphine-antagonistic activity in mice and rats, the tail-flick test was employed, inter alia (J. Pharmacol. Exp. Ther. 72, 74, 1941; modified for antagonistic investigations). The novel compounds of this invention, (B), (C) and (D), showed marked activity in both species, while pentazocine shows a weaker activity, especially in rats.

The mice simultaneously received 12.5 mg/kg. of morphine sulfate and the test compound, in separate subcutaneous injections. Ten mice were used per dosage. The morphine dose used corresponds to the $ED_{80}$, to produce reaction times exceeding the 95% value of the distribution of individual reaction times in control animals (5.5 seconds at N = 572). The criterion for antagonistic effect was a tail-flick reaction within 5.5 seconds after onset of stimulus (triggering).

The rats simultaneously received 6.25 mg/kg. of morphine sulfate and the test compound. The morphine dose employed corresponds to the $ED_{99}$ for the production of reaction times exceeding the 95% value of the distribution of individual reaction times in control animals (6.5 seconds at N = 364). The criterion for antagonistic activity was a tail-flick reaction within 6.5 seconds after onset of stimulus.

The results of the tail-flick test are summarized in Table 2 below.

TABLE 2

| | Morphine Antagonism-Tail-Flick Test $ED_{50}$ (mg/kg) | |
|---|---|---|
| Compound | Mice | Rats |
| B | 5 | 3 |
| C | 1 | 2 |
| D | 1 | 2 |
| Cyclazocine | 0.1 | 0.2 |
| Pentazocine | 5 | 40 |

In a test for the precipitated withdrawal effect on morphine-dependent mice ("precipitated withdrawal jumping" test) according to Saelens et al. (Arch. Int. Pharmacodyn. 190, 213, 1971), the novel compounds of this invention, (C) and (D), demonstrate a considerable activity.

In this test, the animals were made morphine-dependent using an increasing dosage schedule of 5 morphine injections with a total dosage of 400 mg/kg. within 26 hours, wherein the animals received 4 doses of morphine sulfate spaced over a period of 22 hours and a final dose of 125 mg.kg. of morphine base in sesame oil 15 hours prior to administration of the test substances. The test compound was given to dose groups of 8 animals. The antagonist-precipitated withdrawal jumping frequencies were recorded during three 5-minute observation intervals uniformly distributed over 30 minutes after administration of the test compound. Control animals, which were morphine-dependent, showed no withdrawal jumping when treated with NaCl solution. Solvent controls challenged with naloxone (0.39 mg/kg) showed only low jumping frequencies (0.13 ± 0.06/min., N = 80). The criterion for a precipitating effect is a mean jumping frequency of >1/minute.

The results of this test are summarized in Table 3 below.

TABLE 3

| Precipitated Withdrawal Jumping Test Morphine Antagonism-Jumping Test | |
|---|---|
| Compound | $ED_{50}$ (mg/kg.) |
| C | 7 |
| D | 9 |
| B | Inactive[1] |
| Cyclazocine | Inactive[2] |
| Pentazocine | Inactive[3] |
| Naloxone | 0.2 |

[1] 0.1 – 3.13 mg/kg.
[2] 0.55 – 3.13 mg/kg.
[3] 0.78 – 50 mg/kg.

When administering the compounds of this invention and pentazocine subchronically according to the same injection schedule and with the same total dosage as for the evocation of acute physical morphine dependency in mice according to Table 3, no withdrawal jumping is precipitated after administration of the pure antagonist naloxone in doses of up to 100 mg/kg., indicating the absence of a morphine-like physical dependency.

While pentazocine was completely inactive, the inactivity of cyclazocine and compound B of this invention could be attributed to the simultaneous sedative and muscle-relaxant effect of these compounds. This is consistent with the strong muscle-relaxant and anticonvulsant effect of these compounds, as well as compound A, in the maximum electroshock test.

In the maximum electroshock test, the test substances were administered to dose groups of 6 mice. Sinusoidal pulses of 16 milliamperes/50 c.p.s. [Hertz] and 0.2 second duration were delivered transcorneally via silver electrodes. The shock intensity used elicits nonlethal tonic-clonic convulsions in control animals (p <0.01, N = 192). The criterion for protective effect was the absence of the tonic extensor cramp of the hind limbs after shock application (modified test according to Swinyard et al., J. Pharmacol. Exp. Ther. 106, 319, 1952).

The results of this test are summarized in Table 4 below.

TABLE 4

| | Maximal Electoshock Test | |
|---|---|---|
| Compound | | $ED_{50}$ (mg/kg.) |
| A | | 8 |
| B | | 4 |
| Cyclazocine | | 2 |
| Pentazocine | | 17 |
| Chlordiazepoxide | | 12 |

In a test for apomorphine-antogonistic activity, modified according to Janssen et al. ("Arzneim. Forsch."

10, 1003, 1960), on mice, the novel compounds A and B were found to have an only slightly weaker effectiveness than haloperidol and a markedly stronger activity than cyclazocine and pentazocine.

In the apomorphine-antagonism test, mice received simultaneously 1.56 mg/kg. of apomorphine hydrochloride and the test substance in separate subcutaneous injections. Six animals were used per dose. the apomorphine dose corresponds to an $ED_{95}$ for the production of stereotyped behavior in the head region. The criterion for antagonistic effect was the absence of stereotyped movements within an observation period of one minute.

The results of this test are summarized in Table 5 below.

TABLE 5

| Compound | Apomorphine Antagonism $ED_{50}$ (mg/kg.) |
|---|---|
| A | 0.3 |
| B | 0.3 |
| Cyclazocine | 6 |
| Pentazocine | 40 |
| Haloperidol | 0.1 |

The compounds of this invention are useful, for example, for the production of analgetically active drugs in conjunction with the auxiliary substances known and customary in galenic pharmacy.

The compounds of this invention can be employed in admixture with conventional excipients, i.e., pharmaceutically acceptable liquid, semi-liquid or solid organic or inorganic carriers suitable, e.g, for parenteral or enteral application and which do not deleteriously react with the active compound in admixture therewith. Suitable pharmaceutically acceptable carriers include but are not limited to water, salt solutions, alcohols, vegetable oils, polyethylene glycols, gelatine, lactose, amylose magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are unit dosage forms, e.g., tablets, dragees, or capsules having talc and/or a carbohydrate carrier or binder or the like, the carrier preferably being lactose and/or corn starch and/or potato starch; particulate solids, e.g., granules; and liquids and semi-liquids, e.g., syrups and elixirs or the like, wherein a sweetened vehicle is employed. Sustained release compositions can be formulated including those wherein the active compound is protected with differentially degradable coatings, e.g., by microencapsulation, multiple coatings, etc.

Suitable for oral administration are, inter alia, tablets, dragees, capsules, pills, granules, suspensions and solutions. Each unit dose, e.g., each tablespoon of liquid or each tablet, contains, for example, 0.1 – 50 mg. of the effective agent.

Solutions for parenteral application contain, for example, 0.01 – 1% of effective agent in an aqueous solution.

In its process aspect, this invention relates to a process for the production of the benzomorphan derivatives of the general Formula I, wherein a benzomorphan of general Formula II

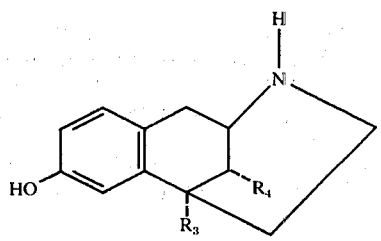

wherein $R_3$ and $R_4$ have the same meanings as indicated in Formula I, a. is reacted in a conventional manner with an epoxide of the general Formula III

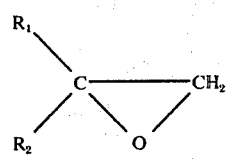

wherein $R_1$ and $R_2$ have the same meanings as in Formula I; or b. with a halohydrin of the general Formula IV

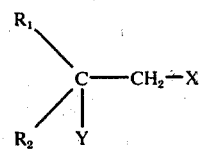

wherein $R_1$ and $R_2$ have the same meanings as in Formula I, and one of X and Y, which are different, is hydroxy and the other is halogen.

The reaction is advantageously conducted in an alcohol, e.g., methanol, ethanol, n- or isopropanol, a butyl alcohol, or an amyl alcohol. The addition of water can have a favorable affect on the reaction. Reaction times vary extensively and are dependent on the reaction components and the reaction temperature. At reaction temperatures of from about 0° to 200° C., reaction times can vary from about 2 hours to 14 days. Temperatures of from 70° to 120° C. are preferred with the reaction times usually being several hours.

In the reaction with a halohydrin of the general Formula IV, it is advantageous to bind the hydrohalic acid liberated in the reaction by the addition of an acid-neutralizing agent, e.g., sodium bicarbonate, potassium bicarbonate or magnesium oxide.

The compounds thus-produced are, in each case, 5,9-cisdialkyl-6,7-benzomorphan derivatives.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

2 g. of (±)-2'-hydroxy-5,9-dimethyl-6,7-benzomorphan and 1 g. of isobutene oxide were dissolved in 9 ml. of methanol. The reaction mixture was heated in a bomb tube to 100° C. for 6 hours. Subsequently, the methanol was distilled off and the residue distilled under vacuum. Under a pressure of 0.001 mm. Hg, at between 178° and 198° C., 2.37 g. of a colorless oil passed over, which was crystallized during treatment with acetone. After recrystallization from the same solvent, the product was 1.3 g. of (±)-2'-hydroxy-2-(2-hydroxy-2-methylpropyl)-5,9-dimethyl-6,7-benzomorphan, m.p. 154°–156° C.

The compound could be dissolved in 1N hydrochloric acid. The solid hydrochloride was obtained from the solution by evaporation.

Analogously to Example 1, the following compounds can also be produced, for example:
(±)-5,9-diethyl-2'-hydroxy-2-(2-hydroxy-2-methylpropyl)-6,7-benzomorphan
(−)-2'-hydroxy-2-(2-hydroxypropyl)-9-methyl-5-propyl-6,7-benzomorphan
(−)-2'-hydroxy-2-(2-hydroxypropyl)-5-methyl-9-propyl-6,7-benzomorphan.

EXAMPLE 2

2 g. of (−)-2'-hydroxy-5,9-dimethyl-6,7-benzomorphan was reacted with isobutene oxide analogously to Example 1. During cooling, 1.6 g. of (−)-2'-hydroxy-2-(2-hydroxy-2-methylpropyl)-5,9-dimethyl-6,7-benzomorphan was crystallized from the reaction solution; m.p. 182°–184° C.

EXAMPLE 3

1.24 g. of (±)-5-ethyl-2'-hydroxy-9-methyl-6,7-benzomorphan was reacted with 0.88 g. of isobutene oxide in 80 ml. of methanol analogously to Example 1. After cooling, the reaction mixture was acidified with 48% aqueous hydrobromic acid and evaporated. The residue, a brown oil, was taken up in a small amount of isopropanol. The mixture was allowed to stand, and 1.3 g. of (±)-5-ethyl-2'-hydroxy-2-(2-hydroxy-2-methylpropyl)-9-methyl-6,7-benzomorphan hydrobromide was thus crystallized from the solution in the form of colorless crystals, m.p. 157°–168° C.

EXAMPLE 4

Analogously to Example 3, (−)-5-ethyl-2'-hydroxy-9-methyl-6,7-benzomorphan was reacted with isobutene oxide to obtain (−)-5-ethyl-2'-hydroxy-2-(2-hydroxy-2-methylpropyl)-9-methyl-6,7-benzomorphan. Melting point of the hydrobromide: 208°–210° C., yield: 72%.

EXAMPLE 5

Analogously to Example 3, (±)-9-ethyl-2'-hydroxy-2-(2-hydroxy-2-methylpropyl)-5-methyl-6,7-benzomorphan hydrobromide was produced; m.p. 205°–210° C.

EXAMPLE 6

1.5 g. of (−)-9-ethyl-2'-hydroxy-5-methyl-6,7-benzomorphan was reacted analogously to Example 3 with 0.72 g. of isobutene oxide and converted into the hydrobromide; the isolated reaction product was 2.4 g. of: (−)-9-ethyl-2'-hydroxy-2-(2-hydroxy-2-methylpropyl)-5-methyl-6,7-benzomorphan hydrobromide, m.p. 210°–211° C.

(−)-9Ethyl-2'-hydroxy-5-methyl-6,7-benzomorphan was produced as follows:

40.0 g. of (±)-9-ethyl-2-benzyl-2'-hydroxy-5-methyl-6,7-benzomorphan was dissolved in 52 ml. of ethanol. A solution of 44.6 g. of (−)-O,O-dibenzoyl-L-tartaric acid in 100 ml. of hot ethanol was added to this solution. The mixture was left in a refrigerator at +3° C. overnight. Then, the thus-precipitated substance was vacuum-filtered, having a dry weight of 20.4 g. Melting point: 197° C.

The crystallized product was suspended in water, and the suspension was rendered alkaline with 0.5N sodium hydroxide solution. The base liberated in this manner was extracted with ether, the ether washed with water, dried over potassium carbonate, and evaporated. There remained 13.0 g. of (+)-9-ethyl-2-benzyl-2'-hydroxy-5-methyl-6,7-benzomorphan in the form of an oil. This product was converted into the hydrobromide, having a melting point of 260°–263° C. after recrystallization from isopropanol.

The mother liquor, from which the dextrorotatory enantiomer had been isolated as the dibenzoyl tartrate, was made alkaline with 0.5N sodium hydroxide solution. The base was isolated as described above, thus obtaining 29.4 g. of a brown, viscous oil. This substance was taken up in 37 ml. of ethanol and mixed with a hot solution of 32.6 g. of O,O-dibenzoyl-D-tartaric acid in 75 ml. of ethanol. After allowing the reaction mixture to stand overnight at +3° C., the thus-precipitated crystallized product was vacuum-filtered and washed three times with a small amount of ice-cold ethanol; the product had a dry weight of 20.6 g.; m.p. 200° C.

From the thus-obtained dibenzoyl tartrate of the levorotatory antipode, the base was liberated in the same manner as the dextrorotatory form; 13.5 g. was isolated.

| | |
|---|---|
| $[\alpha]_D^{20}$ (dextrorotatory form) +81.2° | in 2% acetic acid |
| $[\alpha]_D^{20}$ (levorotatory form) −82.4° | c = 1 |

The hydrobromide of the levorotatory form melted at 260°–263° C. after recrystallization from isopropanol.

16.2 g. of (−)-9-ethyl-2-benzyl-2'-hydroxy-5-methyl6-benzomorphan hydrobromide was dissolved in 200 ml.of dimethylformamide and, with the addition of 0.87 g. of 10% palladium charcoal, hydrogenated at a temperature of 55° C. and under a hydrogen pressure of 60 atmospheres gauge. After shaking the reaction mixture for 5 hours in an autoclave, the reaction was terminated. The catalyst was filtered off and the solvent evaporated under vacuum. The residue was taken up in ethanol and made alkaline with aqueous ammonia. In this procedure, the solution was cooled with ice water. The thus-crystallized base was vacuum-filtered, washed with water, and dried. The crude product was treated with 40 ml. of isopropanol and yielded 7.2 g. of (−)-9-ethyl-2'-hydroxy-5-6,7-benzomorphan, m.p. 260°–264° C. $[\alpha]_D^{20}$ −33.3° in 2% acetic acid, c = 1.

EXAMPLE 7

Analogously to Example 3, 1.85 g. of (+)-5-ethyl-2'-hydroxy-9-methyl-6,7-benzomorphan was reacted with 0.49 ml. of 1,2-epoxypropane. The thus-produced (+)-5-ethyl-2'-hydroxy2-(2-hydroxypropyl)-9-methyl-6,7-benzomorphan hydrobromide had a melting point of 206°–207° C.

EXAMPLE 8

1.60 g. of (−)-2'-hydroxy-5,9-dimethyl-6,7-benzomorphan and 0.546 g. of 1,2-epoxypropane were dissolved in 22 ml. of methanol and heated in a bomb tube for 6 hours to 100° C. 12 ml. of 0.66N hydrobromic acid was added to the cooled-off solution. The mixture was evaporated under vacuum, and the residue was taken up in water. The solution was treated with carbon and brought to pH of approximately 8 with sodium bicarbonate solution. An oily precipitate was thus obtained which was extracted with ether, and the ether was dried and evaporated. The remainder, a light-colored, viscous oil, was crystallized upon trituration. By recrystallization from a very small amount of benzene, 0.7 g. of pure (−)-2'-hyroxy-2-(2-hydroxypropyl)-5,9-dimethyl-6,7-benzomorphan was obtained, m.p. 133°–135° C.

EXAMPLE 9

1 g. (+)-2'-hydroxy-5,9-dimethyl-6,7-benzomorphan and 350 mg of 1,2-epoxybutane were dissolved in 10 ml. of methanol and heated in a bomb tube for 6 hours to 100° C. After cooling, the reaction solution was acidified with aqueous 48% hydrobromide acid, treated with activated carbon, and evaporated. The residue from the evaporation was mixed three times with benzene, and the benzene was again distilled off. The residue, freed in this way from the largest portion of the water, was dried under a pressure of 0.1 mm. Hg column and at 70° C. first over phosphorus pentoxide and then over potassium hydroxide. The residue was crystallized during digestion with isopropanol. After recrystallization from isopropanol, the (±)-2'-hydroxy-2-(2-hydroxybutyl)-5,9-dimethyl-6,7-benzomorphan hydrobromide had a melting point of 125° C.

EXAMPLE 10

In accordance with the procedure of Example 3, 1.85 g. of (−)-5-ethyl-2'-hydroxy-9-methyl-6,7-benzomorphan was reacted with 0.49 ml. of 1,2-epoxypropane. The reaction product was converted into the hydrobromide. The thus-produced (−)-5-ethyl2'-hydroxy-2-(2-hydroxypropyl)-9-methyl-6,7-benzomorphan hydrobromide has a melting point of 205°–206° C. Yield: 1.4 g.

EXAMPLE 11

1.85 g. of (+)-5-ethyl-2'-hydroxy-9-methyl-6,7-benzomorphan, reacted with 0.73 ml. of 1,2-epoxybutane in accordance with the procedure of Example 3, yielded 2.5 g. of (+)-5-ethyl-2'-hydroxy-2-(2-hydroxybutyl)-9-methyl-6,7-benzomorphan hydrobromide. The substance was crystallized with 3% water of crystallization. The melting point of this compound remained poorly defined even after recrystallization from isopropanol.

EXAMPLE 12

1.85 g. of (−)-5-ethyl-2'-hydroxy-9-methyl-6,7-benzomorphan, when reacted with 0.73 ml. of 1,2-epoxybutane according to the process of Example 3, modified only by using acetone in place of isopropanol for recrystallization purposes, yielded 1.0 g. of (−)-5-ethyl-2'-hydroxy-2-(2-hydroxybutyl)-9-methyl-6,7-benzomorphan hydrobromide, m.p. 158°–162° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A benzomorphan of the formula

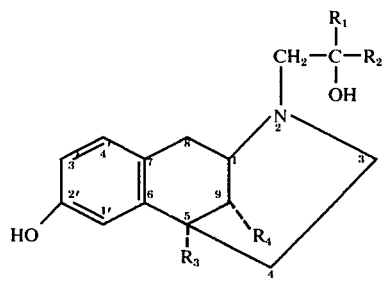

wherein $R_1$ is H, $CH_3$, $C_2H_5$; $R_2$ is $CH_3$ or $C_2H_5$; and $R_3$ and $R_4$ each are alkyl of 1–4 carbon atoms, in free base form or as an acid addition salt thereof with a physiologically acceptable acid.

2. A hydrochloride acid addition salt of claim 1.

3. Compounds of claim 1, (±)-2'-hydroxy-2-(2-hydroxy-2-methylpropyl)-5,9-dimethyl-6,7-benzomorphan and the hydrochloride thereof.

4. The compound of claim 1, (−)-2'-hydroxy-2-(2-hydroxy-2-methylpropyl)-5,9-dimethyl-6,7-benzomorphan.

5. The compound of claim 1, (±)-5ethyl-2'-hydroxy-2-(2-hydroxy-2-methylpropyl)-9-methyl-6,7-benzomorphan hydrobromide.

6. The compound of claim 1, (−)-5-ethyl-2'-hydroxy-2-(2-hydroxy-2-methylpropyl)-9-methyl-6,7-benzomorphan hydrobromide.

7. The compound of claim 1, (±)-9-ethyl-2'-hydroxy-2-(2-hydroxy-2methylpropyl)-5-methyl-6,7-benzomorphan hydrobromide.

8. The compound of claim 1, (−)-9-ethyl-2'-hydroxy-2(2-hydroxy-2-methylpropyl)-5-methyl-6,7-benzomorphan hydrobromide.

9. The compound of claim 1, (+)-5-ethyl-2'-hydroxy-2-(2-hydroxypropyl)-9-methyl-6,7-benzomorphan hydrobromide.

10. The compound of claim 1, (−)-2'-hydroxy-2-(2-hydroxypropyl)-5,9-dimethyl-6,7-benzomorphan.

11. The compound of claim 1, (±)-2'-hydroxy-2-(2-hydroxybutyl)5,9-dimethyl-6,7-benzomorphan hydrobromide.

12. The compound of claim 1, (−)-5-ethyl-2'-hydroxy-2-(2-hydroxypropyl)-9-methyl-6,7-benzomorphan hydrobromide.

13. The compound of claim 1, (+)-5-ethyl-2'-hydroxy-2-(2-hydroxybutyl)-9-methyl-6,7-benzomorphan hydrobromide.

14. The compound of claim 1, (−)-5-ethyl-2'-hydroxy-2-(2-hydroxybutyl)-9-methyl-6,7-benzomorphane hydrobromide.

15. The compound of claim 1, (±)-5,9-diethyl-2'-hydroxy-2-(2-hydroxy-2-methylpropyl)-6,7-benzomorphan.

16. The compound of claim 1, (−)-2'-hydroxy-2-(2-hydroxypropyl)-9-methyl-5-propyl-6,7-benzomorphan.

17. The compound of claim 1, (−)-2'-hydroxy-2-(2-hydroxypropyl)-5-methyl-9-propyl-6,7-benzomorphan.

18. A pharmaceutical composition in unit dosage form comprising a non-toxic, analgesic amount per unit dosage of a compound of claim 1 in combination with a pharmaceutically acceptable carrier.

* * * * *